(12) United States Patent
Carlezon, Jr.

(10) Patent No.: US 6,528,518 B2
(45) Date of Patent: Mar. 4, 2003

(54) TREATMENT OF DEPRESSION WITH KAPPA RECEPTOR ANTAGONISTS

(75) Inventor: William A. Carlezon, Jr., Belmont, MA (US)

(73) Assignee: The McLean Hospital Corporation, Belmont, MA (US)

( * ) Notice: Subject to any disclaimer, the term of this patent is extended or adjusted under 35 U.S.C. 154(b) by 0 days.

(21) Appl. No.: 10/027,135

(22) Filed: Dec. 20, 2001

(65) Prior Publication Data

US 2002/0091075 A1 Jul. 11, 2002

Related U.S. Application Data

(60) Provisional application No. 60/258,029, filed on Dec. 21, 2000.

(51) Int. Cl.[7] .......................... A61K 31/44; A61K 31/40
(52) U.S. Cl. ........................................ 514/279; 514/428
(58) Field of Search ................................ 514/279, 428

(56) References Cited

PUBLICATIONS

Filliol, et al., "Mice deficient for delta– and muopiod receptors exhibit opposing alterations of emotional responses" *Nature Genetics* 25:195–200 (Jun. 2000).

Makino et al., "Involvement of central opioid systems in human interferon–alpha induced immobility in the mouse forced swimming test" *Br. J. Pharmacol* 130:1269–1274 (Jul. 2000).

Carlezon et al., "Regulation of cocaine reward by CREB" *Science* 282:2272–2275 (Dec. 1998).

Bals–Kubik et al., "Neuroanatomical sites mediating the motivational effects of opioids as mapped by the conditioned place preference paradigm in rats" *The Journal of Pharmacology and Experimental Therapeutics* 264:489–495 (1992).

Pan, "μ–opposing actions of the κ–opioid receptor" *TiPS* 19:94–98 (1998).

Pfeiffer et al., "Psychotomimesis mediated by κ opioid receptors" *Science* 233:774–776 (1986).

Bals–Kubik et al., "Evidence that the aversive effects of opioid antagonists and κ antagonists are centrally mediated" *Psychopharmacology* 98:203–206 (1989).

Schmidhammer, "3 opioid receptor antagonists" *Progress in Medicinal Chemistry* 35:83–133 (1998).

Svingos et al., "Cellular sites for dynorphin activation of κ–opioid receptors in the rat nucleus accumbens shell" *The Journal of Neuroscience* 16:1804–1813 (1999).

Tortella and DeCoster, "Kappa opioids: the therapeutic considerations in epilepsy and CNS injury" *Clinical Neuropharmacology* 17:403–416 (1994).

*Primary Examiner*—William R. A. Jarvis
(74) *Attorney, Agent, or Firm*—Clark & Elbing LLP

(57) ABSTRACT

The invention features the treatment of depression using kappa opioid receptor antagonists.

21 Claims, 7 Drawing Sheets

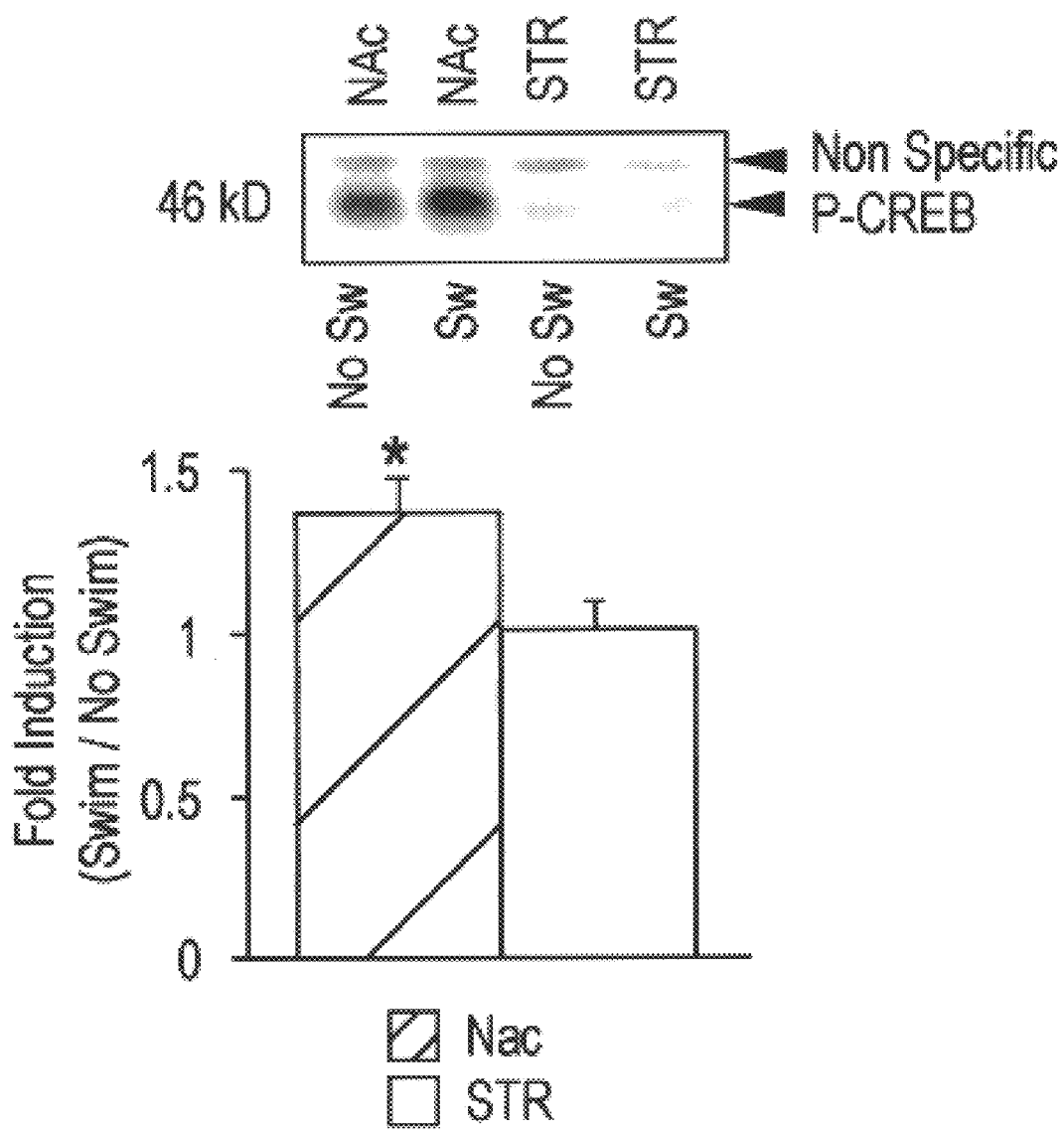

TREATMENT OF DEPRESSION WITH KAPPA RECEPTOR ANTAGONISTS

CROSS REFERENCE TO RELATED APPLICATIONS

This application claims priority from U.S. Provisional Application Serial No. 60/258,029, filed Dec. 21, 2000.

BACKGROUND OF THE INVENTION

The mesolimbic dopamine system, which originates in the ventral tegmental area and projects to the nucleus accumbens (NAc), is involved in the pleasurable (hedonic) and rewarding effects of a variety of substrates, including drugs of abuse, food, and sexual behavior. Drugs of abuse cause complex neuroadaptations in this system, some of which are associated with altered drug sensitivity. One neuroadaptation involves cAMP response element-binding protein (CREB), a transcription factor that is activated in striatal regions by psychostimulants. CREB in the NAc appears to regulate the rewarding and aversive effects of cocaine. Stimulation of cAMP-dependent protein kinase A (PKA), which activates CREB, in the NAc decreases cocaine reward. Similarly, elevation of CREB expression in the NAc decreases cocaine reward and makes low doses of the drug aversive. Conversely, blockade of PKA activity or overexpression of a dominant-negative CREB, which functions as a CREB antagonist, in the NAc increase cocaine reward. These findings suggest that CREB activation in the NAc counteracts drug reward and increases drug aversion.

Cocaine alters neuronal excitability and neurotransmitter levels in the brain, particularly the mesolimbic dopamine system. Cocaine withdrawal is accompanied by signs of depression and other mood disorders in humans. The biological basis of mood disorders like depression is not understood, but may be caused by genetic and environmental factors. Physically and emotionally stressful events can also influence the etiology of depression, possibly causing subtle brain changes and alterations in gene expression. Thus, depression may have an important acquired component, caused by neuroadaptations in response to environment and experience.

The therapeutic actions of antidepressants appear to involve neuroadaptations. Most antidepressant treatments (including tricyclic and atypical antidepressants, selective serotonin reuptake inhibitors, electroconvulsive therapy) have common actions on components of the cAMP pathway. Common actions include activation of PKA and the transcription factor CREB in the hippocampus, a brain region associated with emotion. CREB plays a critical role in the expression of numerous genes. Understanding causal relations among CREB function, gene expression, and the therapeutic effects of antidepressants might provide explanations for why antidepressants require sustained treatment for effectiveness. Additionally, because some genes regulated by CREB may be therapeutic while others may be pathophysiological, a more general understanding of the role CREB in behavior might help to elucidate the biological basis of depressive syndromes.

Many of the researchers studying depression are focused on the hippocampus. Many antidepressants increase the level of CREB in the hippocampus. In this region, it is believed that increasing CREB activity is beneficial, because CREB controls some growth factors (e.g., BDNF) in the brain. However, there is no evidence that increasing CREB in the hippocampus is associated with the therapeutic effects of antidepressants.

Although much research on the molecular mechanisms of depression and antidepressant actions has focused on the hippocampus, the NAc may also have relevance. This basal forebrain region is innervated by dopamine neurons of the ventral tegmental area, as well as by noradrenergic and serotonergic inputs. The NAc contributes importantly to the pleasurable effects of food, sexual behavior, novelty, and addictive drugs.

Most current antidepressants act primarily on brain levels of noradrenaline or serotonin. There is some evidence that dopamine systems might be involved in depressive syndromes. Blocking dopamine receptors in the brain causes anhedonia (a decreased ability to experience pleasure), a defining feature of depression. Nomifensine, a dopamine reuptake inhibitor, was a clinically effective antidepressant, further implicating dopaminergic dysfunction in depression. Nomifensine was taken off the market because it caused lethal allergic reactions in some people.

SUMMARY OF THE INVENTION

The present invention provides methods for treating depression and other psychiatric diseases associated with symptoms of depression. The invention is based, in part, on discovery that stressors that cause symptoms of depression in rats increase the activation of CREB in the nucleus accumbens. CREB activation results in the activation of the prodynorphin gene, which encodes the opioid peptide dynorphin. Dynorphin is an agonist of the kappa opioid receptors in the brain, and enhances symptoms of depression. The kappa receptor antagonists norBNI and GNTI demonstrate antidepressant effect in rats, which is mediated by a disinhibition of dopamine release in the nucleus accumbens.

The invention features, in one aspect, a method for treating a depressive disorder, or reducing cAMP response element-binding protein (CREB) activation in a mammal, e.g., a human patient, by administering an effective amount of a kappa receptor antagonist. Kappa receptor antagonists are particularly useful for treating major depression, dysthymia, bipolar disorder (manic depression), and post traumatic stress disorder; however, any psychologic or psychiatric disorder having symptoms that include depression are amenable to treatment according to the present methods. The kappa receptor antagonists can bind either reversibly or irreversibly.

The kappa receptor antagonists can be administered systemically, including, for example, by intravenous, intramuscular, or subcutaneous injection, orally, or by topical or transdermal application, provided that the kappa receptor antagonist is capable of penetrating the blood-brain barrier sufficiently to be effective. Alternatively, the kappa receptor antagonists can be centrally administered using, for example, by an intrathecal, intracerebroventricular, or intraparenchemal injection. Useful kappa receptor antagonists include, for example, nor-binaltorphimine (norBNI), GNTI (5'-guanidinyl-17-(cyclopropylmethyl)-6,7-dehydro-4,5α-epoxy-3,14-dihydroxy-6,7-2',3'-indolomorphinan), and DIPPA (2-(3,4-dichorophenyl)-N-methyl-N-[(IS)-1-(3-isothiocyanatophenyl)-2-(1-pyrrolidinyl)ethyl]acetamide).

By "depressive disorder" is meant any psychologic or psychiatric disorder which is associated with symptoms of depression. Treatable depressive disorders can be characterized by an inhibition or reduction of dopaminergic function in the nucleus accumbens, e.g., major depression, dysthymia, bipolar disorder (manic depression), and post-traumatic stress disorder.

By "kappa antagonist" is meant any chemical compound which has affinity for the kappa opioid receptor and attenuates or prevents the binding or physiologic response associated with dynorphin binding. Kappa antagonists which are useful according to this invention can be competitive or non-competitive inhibitors of dynorphin binding. Inverse agonists, compounds which cause the opposite effect of the agonist, can be used in place of the kappa antagonists in any of the methods of this invention. Preferably, kappa antagonists (or inverse agonists) bind with a dissociation constant of less than $10^{-7}, 10^{-8}, 10^{-9}, 10^{-10}, 10^{-11}, 10^{-12}$, or even $10^{-15}$ moles/L.

BRIEF DESCRIPTION OF THE DRAWINGS

FIGS. 3A–3C are bar graphs of the pharmacological and molecular characterization.of the forced swim test (FST). (A) Latencies to become immobile (mean±SEM) on the re-test day in the FST are increased by DMI ($F_{3,47}=5.67$, $P<0.01$) and FLX ($F_{3,44}=3.38$, $P<0.05$). (B) Activity (mean±SEM) is decreased by high doses of DMI ($F_{3,36}=7.92$, $P<0.01$) and FLX ($F_{3,25}=10.6$, $P<0.01$). *$P<0.05$, ** $P<0.01$ compared to vehicle (0 mg/kg) groups, Fisher's t-test, 8–14 rats per group. (C) Western blot of P-CREB in NAc (shell) and striatum (STR) after 15 min of forced swimming (Sw). Control rats did not undergo swimming (No Sw). Forced swimming significantly increased P-CREB expression in the NAc but had no effect in the STR ($t_{10}=2.48$, $P<0.05$). Data are expressed as the ratio (mean±SEM, 6 rats per group) of P-CREB expression in the Sw and No Sw groups for each region. *$P<0.05$, Student's t-test.

DETAILED DESCRIPTION

The nucleus accumbens (NAc) is a limbic region involved in the pleasurable (hedonic) effects of food, sexual behavior, and addictive drugs. Although a diminished ability to experience pleasure (anhedonia) is a symptom of clinical depression, little is known about the involvement of the NAc in mood disorders. We have discovered that increased expression of CREB in this region causes signs of anhedonia and despair in rats. Symptoms are alleviated by local disruption of CREB function, or by blockade of brain receptors for dynorphin, a neuropeptide regulated by CREB. This work demonstrates that kappa receptor antagonists can be used to reduce CREB activation in the nucleus accumbens, resulting in the alleviation of symptoms of depression. Accordingly, kappa receptor antagonists are useful for treating depression, bipolar disorder, and other conditions associated with symptoms of depression.

Viral Vector-mediated Gene Transfer cDNAs for CREB, mCREB, and LacZ were inserted into the herpes simplex virus (HSV) amplicon HSV-PrpUC and packaged into virus using the helper Sld1.2, according to the method of Neve et al. (Neuroscience 79:435–447, 1997). Final vector stocks had a titer of approximately $4.0 \times 10^7$ units/ml. Transgene expression caused by these vectors is maximal 3–4 days after treatment and is virtually absent by day 10. The mCREB vector encodes a mutant form of the CREB protein which acts in a dominant negative manner.

Figure 1A:
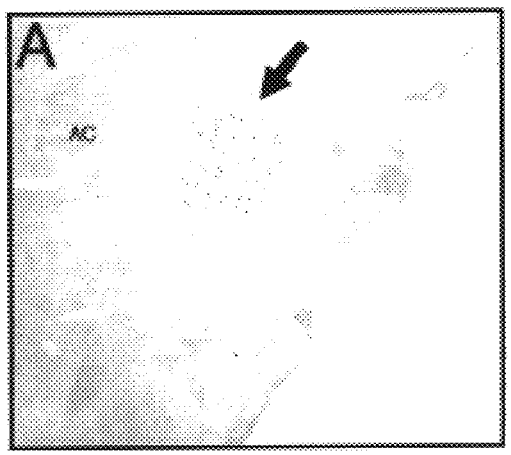
FIGS. 1A–1C are photomicrographs of the NAc after gene transfer. (A) Expression of CREB 4 days after microinjection of HSV-CREB into the left NAc shell (×40) (5). Arrow indicates injection site. (B) Higher magnification (×200) of the injection site in (A), confirming nuclear localization of CREB expression. Expression of mCREB (dominant negative CREB) is indistinguishable from that of CREB (5). (C) An adjacent, Nissl-stained slice from the same brain. AC, anterior commissure.
Figure 1B:
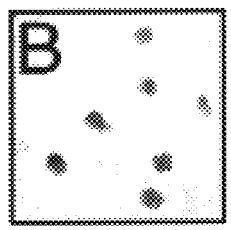
Figure 1C:
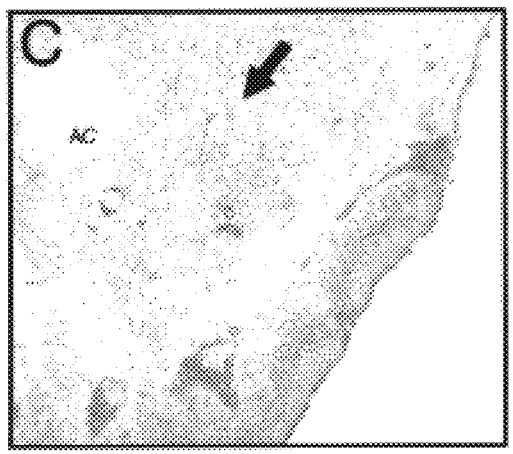

Microinjections of HSV-CREB, HSV-mCREB, or HSV-LacZ produced approximately 2000 transgene-labeled cells in each NAc three days after gene transfer. This was reduced by day 5 (FIG. 1A) or day 11, the completion of behavioral testing, demonstrating the transient nature of transgene expression caused by HSV vectors. Transgene expression was limited to an area of about 1.5 mm in diameter and occurred only in neurons. CREB and mCREB immunoreactivity was restricted to the cell nucleus. The vectors caused minimal damage and was indistinguishable from microinjection of the vehicle, 10% sucrose (FIG. 1C).

Cocaine Place Conditioning

To examine how CREB in the NAc affects the pleasurable effects of cocaine in rats, we used herpes simplex virus (HSV)-mediated gene transfer to increase or block its function within this brain region. Elevated CREB expression in the NAc increases transcription of CREB-regulated genes, such as prodynorphin.

Place conditioning was performed in a three compartment apparatus. During screening (day 0), rats were placed in the small (12×18×33 cm) central compartment and were allowed to explore the entire apparatus for 30 minutes. The compartments differed in floor texture, wall striping, and lighting. Rats showing no baseline preference were used for the study. Rats received bilateral microinjections (2.0 μl per side) at AP+1.7 mm, Lat±2.3 mm, and DV 6.8 mm. Injections were made over 10 minutes using a 26 gauge needle.

Behavioral testing began on day 3 after vector injection. On the first conditioning trial of each day, rats received saline (1 ml/kg, i.p.) and were confined to one of the large (24×18×33 cm) side compartments of the apparatus. After three hours, rats received cocaine (1.25 mg/kg, i.p.) and were confined to the other side compartment. Three types of conditioning session were used: a one hour pairing session where the animals were placed immediately into the apparatus immediately after treatment for one hour; 15 minute pairing session where the animals were placed immediately into the apparatus immediately after treatment for 15 minutes; or a delayed pairing session where the animals were placed in the apparatus for one hour following a 15 minute delay from drug exposure.

Figure 2B:
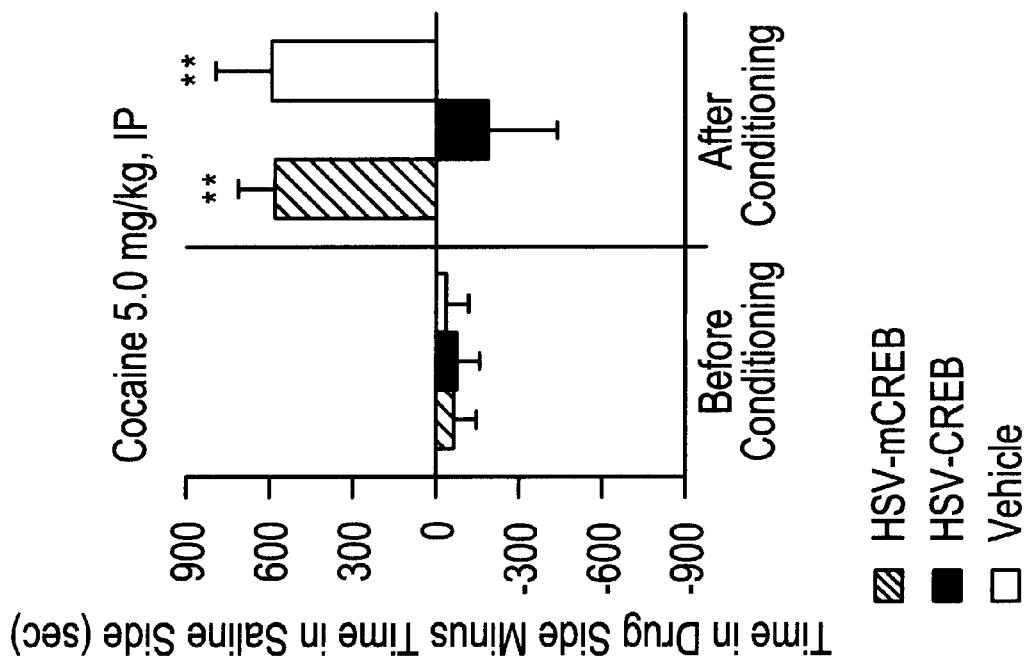
FIGS. 2A and 2B are bar graphs showing the anhedonic effects of CREB gene transfer on cocaine-associated place conditioning. (A) At a threshold dose of cocaine (1.25 mg/kg, i.p.), changes in the time spent in cocaine-associated environments (mean±s.e.m, 6–9 rats per group) depended on viral vector treatment ($F_{2,56}=3.38$, $P<0.05$) and conditioning procedure ($F_{2,56}=14.6$, $P<0.01$). In 1 hr conditioning sessions, rats given intra-NAc (shell) microinjections of HSV-mCREB spent more time in cocaine-associated environments than rats given similar microinjections of vehicle (10% sucrose) or HSV-CREB. Shortening the conditioning sessions to 15 min eliminated differences between rats in the HSV-mCREB and vehicle groups only. Differences persisted when 1 hr conditioning sessions were delayed by 15 min. *$P<0.05$,  $P<0.01$ compared to HSV-mCREB groups, Fisher's t-test. (B) A higher dose of cocaine (5.0 mg/kg, IP) established maximal (~600 sec) place preferences in the. HSV-mCREB and vehicle groups, but had no effect in the HSV-CREB group (treatment x days interaction: $F_{2,24}=4.42$, $P<0.05$). Data are expressed as the time spent in the cocaine-associated environments (mean±SEM, 8–11 rats per group).  $P<0.01$ compared to before conditioning, Fisher's t-test.
Figure 2A:
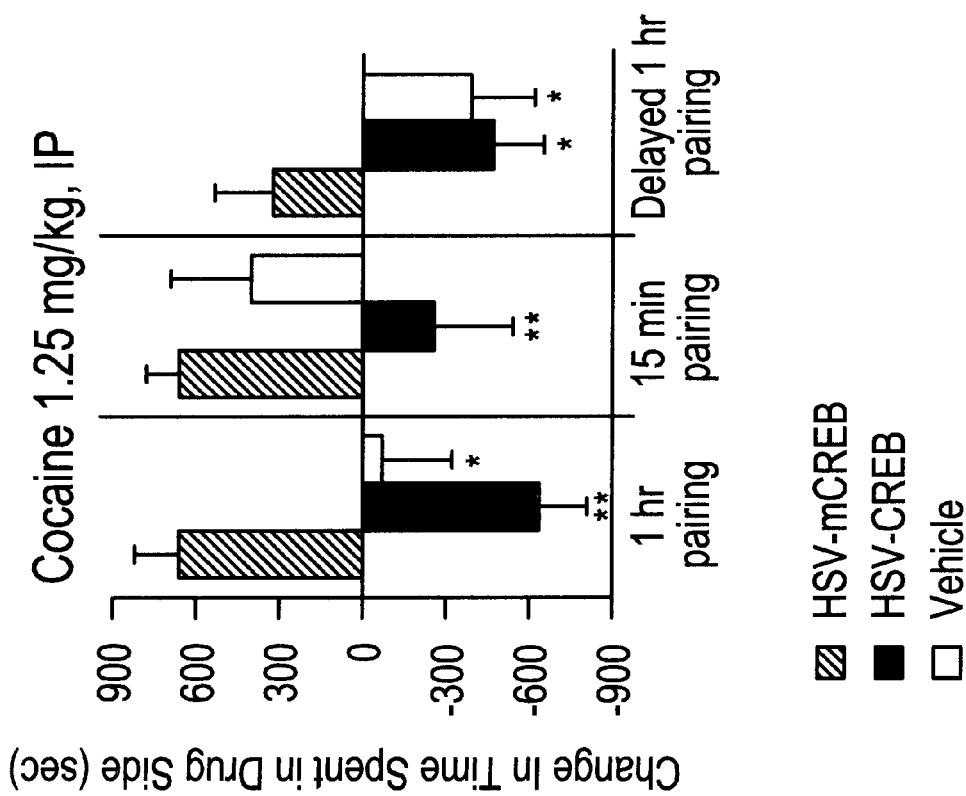

In the place-conditioning assay, rats tend to approach environments associated with rewarding drug effects and avoid environments associated with aversive drug effects or drug withdrawal. At a threshold dose of cocaine (1.25 mg/kg), changes in the time spent in cocaine-associated environments depended on viral vector treatment and conditioning procedure (FIG. 2). In one hour conditioning sessions, rats injected with mCREB into the NAc spent more time in cocaine-associated environments than rats similarly treated with HSV-CREB or vehicle. These data suggest that disruption of CREB function in the NAc increases the pleasurable (rewarding) effects of cocaine.

To better understand the effects of CREB and mCREB, we shortened the conditioning sessions to 15 min to coincide with peak cocaine effects. Shortening the conditioning session to 15 minutes increased the amount of time that control rats spent in the cocaine-associated environment, suggesting peak cocaine reward during this period. Under these conditions, place preferences did not increase further in rats given HSV-mCREB, consistent with observations that there are upper limits to the magnitude of place preferences. Even under these optimized conditions, cocaine was not pleasurable in rats with elevated CREB in the NAc. The conditioning sessions delayed by 15 minutes prevented association of the peak cocaine reward period from associating with the apparatus. In control and HSV-CREB rats, the cocaine appeared aversive. Additionally, even elevated cocaine doses (5.0 mg/kg) were not pleasurable in rats with elevated CREB expression in the NAc. The delayed regimen did not reverse the cocaine association of the mCREB group. Together, these data demonstrate that elevated CREB expression in the NAc causes anhedonia.

Forced Swim Test (FST)

Another symptom of clinical depression that can be modeled in rats is despair, a feeling of hopelessness. Symptoms of despair can be induced in rats using the forced swim test (FST), a highly validated model used to study antidepressant treatments.

The FST is a two day procedure in which rats swim under conditions in which escape is not possible. On the first day, the rats are forced to swim for 15 minutes. The rats initially search for an escape from the water, but eventually adopt a posture of immobility in which they make only the movements necessary to keep their heads above water. Upon re-testing one day later, latencies to become immobile—an indicator of how rapidly the rats "give up" in response to a familiar stressor—are decreased, which is inferred as despair. Standard antidepressants such as desipramine (DMI) and fluoxetine (FLX) extend latencies to become immobile. Drug efficacy in this animal model is predictive of antidepressant efficacy in humans.

To examine the effects of gene transfer and antidepressant therapy on locomotor activity, groups of rats were tested for 1 hour in automated activity chambers 24 hours after the first FST.

Figure 3A:
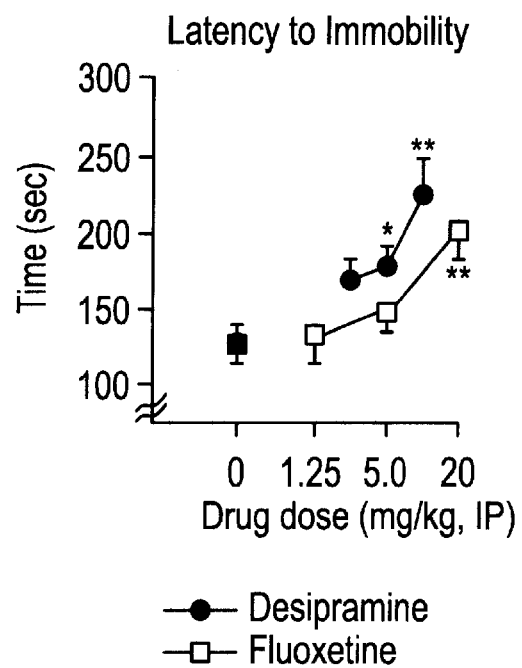
Figure 3B:
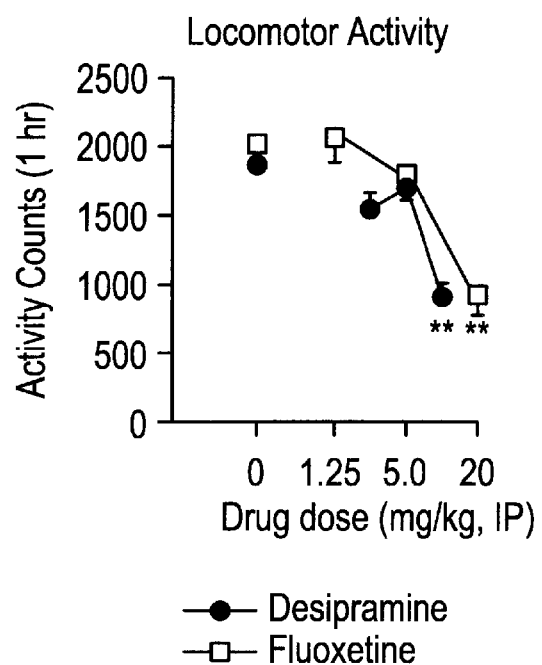
Figure 4A:
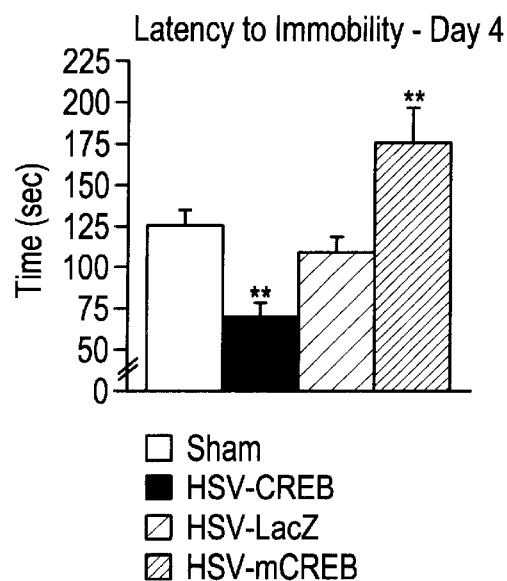
FIGS. 4A–4D are bar graphs showing performance in the FST after CREB gene transfer. (A) Latencies to become immobile in the FST depended upon viral vector treatment ($F_{3,43}=8.83$, $P<0.01$) when transgene expression is maximal (days 3–4). Latencies were decreased in rats treated with HSV-CREB, and increased in rats given HSV-mCREB. HSV-LacZ had no effect. Data are expressed as latencies (mean±SEM, in sec) during the 5 min re-test on day 4. **$P<0.01$ compared to sham, Fisher's t-test. (B) There were no group differences when activity rather than swimming was quantified during re-testing, or (C) when the FST was conducted after transgene expression had diminished (days 10–11). Data in (C) are expressed as latencies (mean ±SEM, in sec) during the 5 min re-test on day 11. (D) Gene transfer did not affect rat weights, but rats re-tested on day 11 weighed more than rats re-tested on day 4 ($t_{73}=10.6$, $P<0.01$).
Figure 4B:
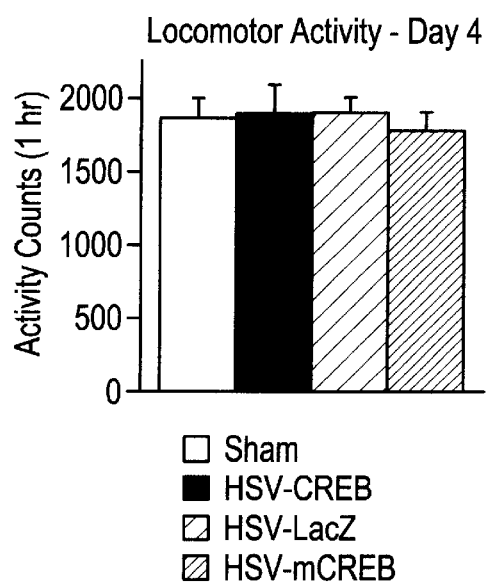
Figure 4C:
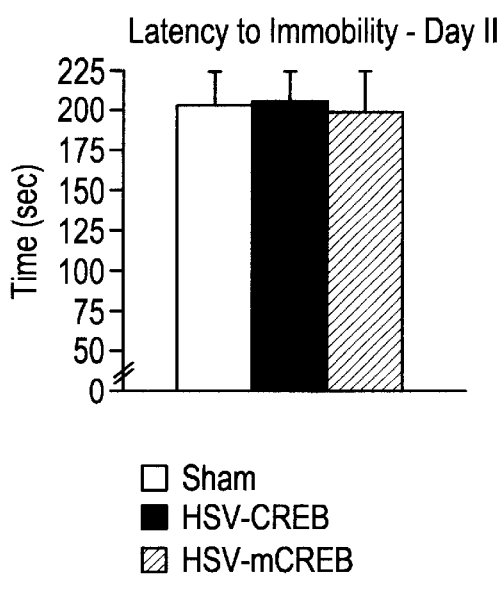
Figure 4D:
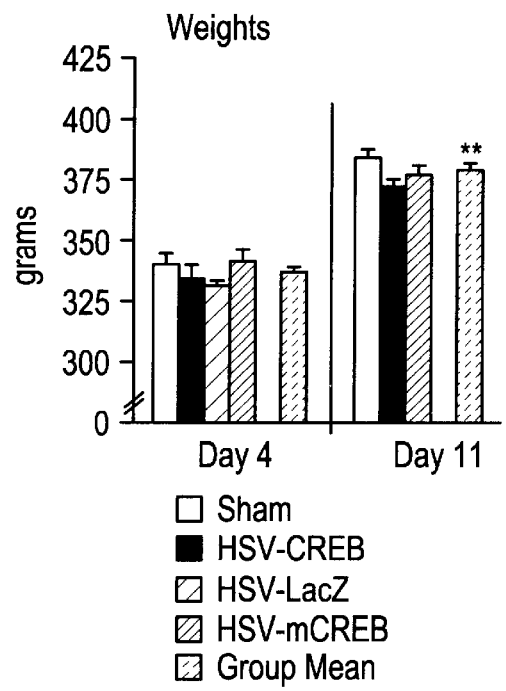

Latencies to become immobile in rats microinjected with HSV-CREB were significantly shorter than control rats (FIG. 4A), and opposite to the effect of standard antidepressant therapy using either desipramine or fluoxetine (FIG. 3). Conversely, the latencies of rats microinjected with HSV-mCREB were significantly longer than those of control rats, consistent with antidepressant therapy. These differences did not result from non-specific depression of locomotor activity as all groups performed equally in the activity chambers (FIG. 4B).

Alterations in CREB function were responsible for the behavioral effects observed during testing on days 3 and 4. No differences were observed among groups of animals tested in the FST on days 10 and 11, after transgene expression had diminished. As expected, alterations in CREB activity have only a transient effect on behavior, consistent with its role in an intracellular signal transduction pathway.

Untreated rats were used to examine the effect of the FST on CREB phosphorylation in the NAc and dorsal striatum. Animals underwent the first day of FST and levels of P-CREB, the phosphorylated and activated form of CREB, were analyzed by Western blotting of tissue punches obtained from the appropriate brain regions. FST caused significant increases in P-CREB within the NAc, but not the caudate-putamen (FIG. 3C).

Together, these findings demonstrate that activation of CREB is a specific effect of swim stress on gene expression in brain pleasure systems, rather than a non-specific (motoric) consequence of swimming. It also suggests that CREB in the NAc is a "molecular trigger" for symptoms of depression.

Kappa Receptor Antagonists: Performance in the FST

Figure 5:
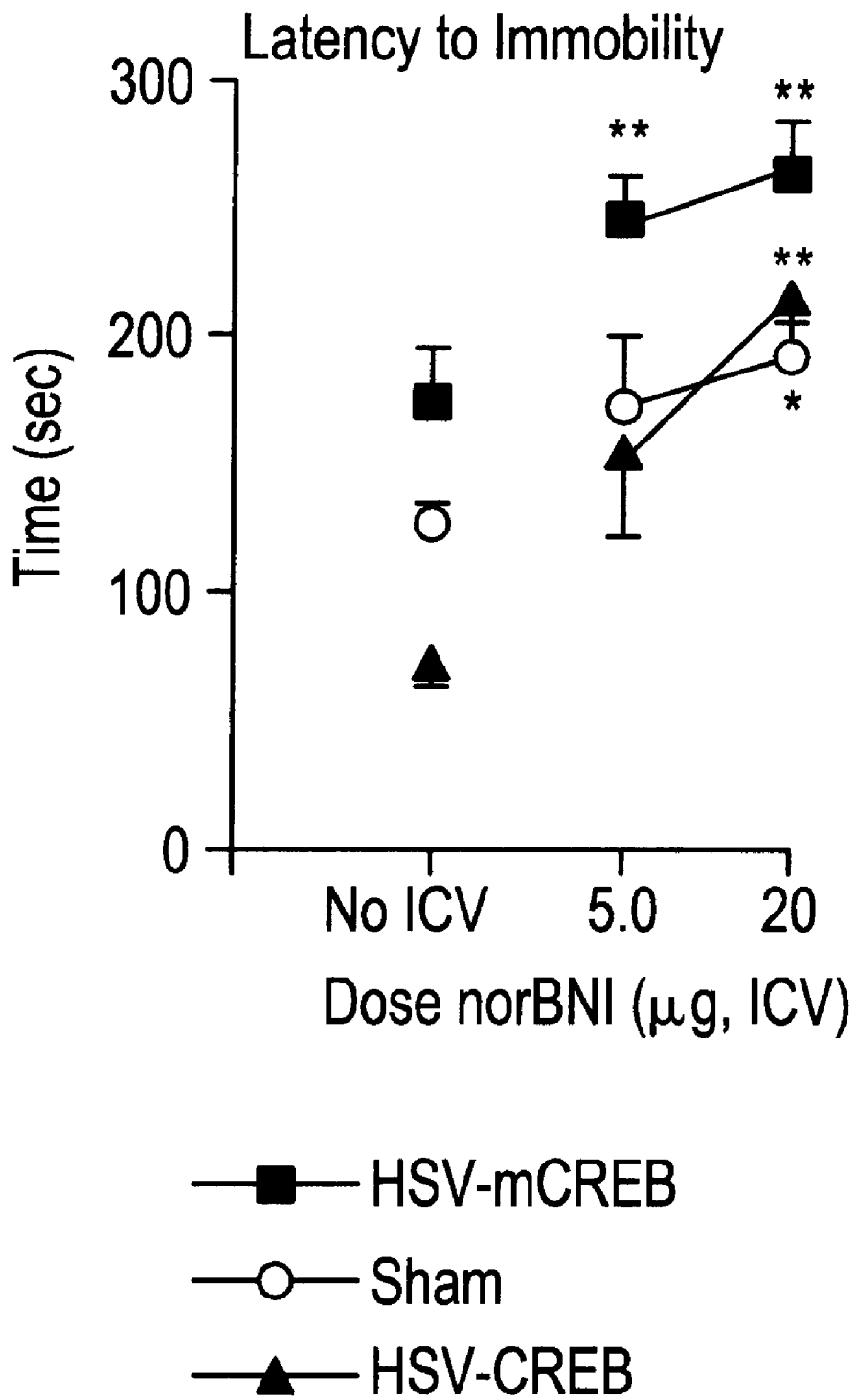
FIG. 5 is a graph showing the effect of norBNI (5.0 or 20 µg, ICV) on FST performance. Treatment with norBNI dose-dependently increased latencies to become immobile (mean±SEM) in each group (main effect of dose: $F_{2,69}=14.1$, $P<0.01$; main effect of vector: $F_{2,69}=11.7$, $P<0.01$). *$P<0.05$, **$P<0.01$, Fisher's t-tests, compared to no ICV for each treatment.
Figure 6A:
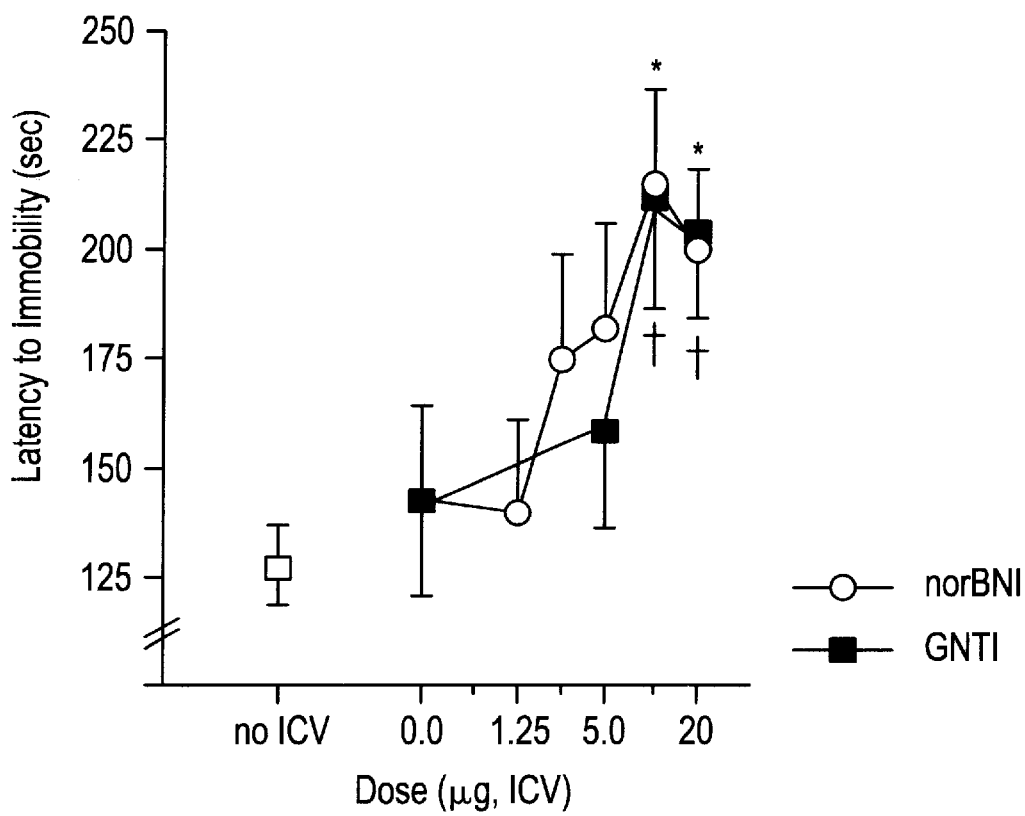
FIG. 6A is a graph comparing the effect of norBNI and GNTI in the forced swim test. GNTI was equipotent to norBNI for increasing latencies to become immobile in the FST. Both treatment groups exhibited significantly longer latencies than the control group.
Figure 6B:
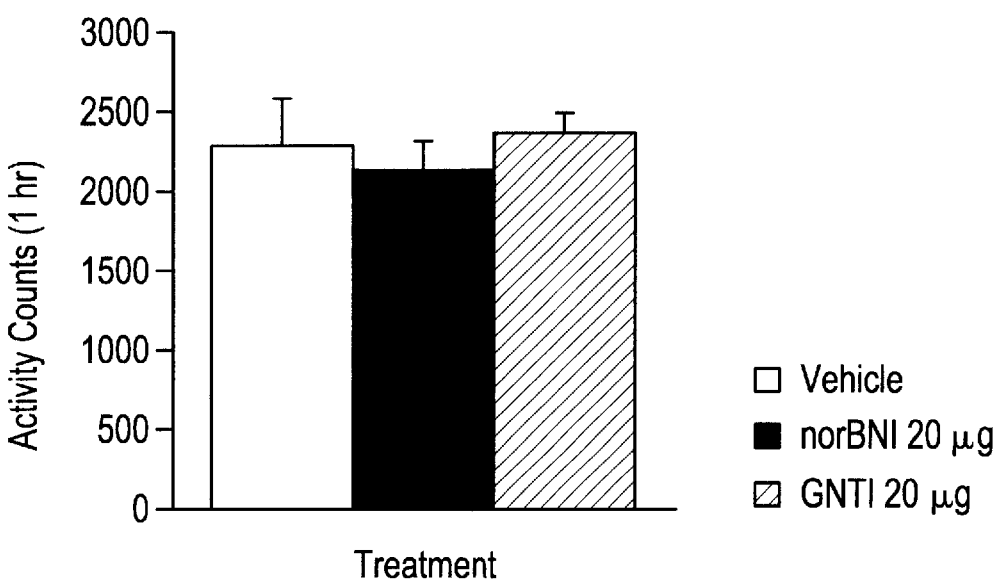
FIG. 6B is a graph comparing the locomotor effects following ICV injection of either a kappa receptor antagonist or vehicle control. No statistically significant differences were observed.

CREB-mediated increases in dynorphin expression within the NAc underlie the decreases in the pleasurable effects of cocaine in the place conditioning paradigm: blockade of brain kappa opioid receptors (on which dynorphin acts) eliminates CREB-induced aversion to cocaine. To determine whether disruption of dynorphin function also eliminates CREB-induced despair in the FST, brain kappa receptors were blocked with either norBNI (nor-binaltorphimine) or GNTI (5'-guanidinyl-17-(cyclopropylmethyl)-6,7-dehydro-4,5α-epoxy-3,14-dihydroxy-6,7-2',3'-indolomorphinan). Both norBNI and GNTI were administered via intraventricular injection because neither compound can penetrate the blood-brain-barrier following systemic administration. Treatment with norBNI dose-dependently increased latencies to become immobile, an antidepressant-like effect (FIG. 5). GNTI was roughly equipotent to norBNI for extending immobility latencies in the FST (FIG. 6A). Neither compound affected non-specific motor function (FIG. 6B). Together, these findings demonstrate that activation of CREB in the NAc triggers molecular adaptations that regulate certain symptoms of depression. As with CREB-induced anhedonia, dynorphin is critically involved in CREB-induced despair. Furthermore, they indicate that disruption of CREB function in this region may have antidepressant actions.

Anti-Depressant Therapy Using Kappa Receptor Antagonists

In humans, cocaine withdrawal causes symptoms of dysphoria and depression. In rats, cocaine withdrawal is associated with hypofunction of the mesolimbic system. Antidepressants can attenuate symptoms of cocaine withdrawal, suggesting that the symptoms involve signs of depression. Accordingly, therapeutics which result in a down-regulation of CREB expression or function are useful for alleviating the withdrawal symptoms caused by the cessation of cocaine, or any other drug of abuse.

CREB regulates many genes, including dynorphin, a neuropeptide that acts as a kappa receptor agonist. Synthetic kappa agonists cause dysphoria in humans, and intra-NAc microinjections of these agents cause place aversions in rats. In the experiments described above, both norBNI and GNTI dose-dependently increased latencies to become immobile in the FST, a paradigm known to cause CREB activation in the NAc. Together, these data demonstrate that kappa receptor antagonists are useful for reducing CREB activation in NAc and alleviating symptoms associated with depression.

Both norBNI and GNTI were administered by intracerebroventricular (i.c.v.) injection because neither compound can penetrate the blood-brain-barrier following systemic administration. In humans, injection of this drug into the brain is feasible, as the administration of other drugs by such injection is known. Alternatively, the drug can be formulated with known agents that facilitate crossing of the blood/brain barrier, as has been done with other agents. Further, in patients, e.g., recent stroke victims, who both suffer from depression and have temporarily compromised blood/brain barriers, the drug is expected to enter the brain after administration into the circulation, e.g., by IV injection or infusion.

The drug is administered to humans in dosages extrapolated from the dosages found to be effective in rats as described herein, admixed with a pharmaceutically acceptable carrier such as sterile water or saline solution.

Other kappa antagonists useful in the method of the invention can be identified by conducting a screening test for kappa receptor blocking ability as described, for example, by Spangler et al. (*Neurosci. Lett.* 153:232, 1993).

What is claimed is:

1. A method for treating a depressive disorder in a mammal, said method comprising administering to said mammal an effective amount of a kappa receptor antagonist.
2. The method of claim 1, wherein said mammal is a human.
3. The method of claim 2, wherein said depressive disorder is major depression.
4. The method of claim 2, wherein said depressive disorder is bipolar disorder.
5. The method of claim 2, wherein said depressive disorder is dysthymia.
6. The method of claim 2, wherein said depressive disorder is post-traumatic stress disorder.
7. The method of claim 2, wherein said kappa receptor antagonist is administered systemically.
8. The method of claim 2, wherein said kappa receptor antagonist is administered by intracerebroventricular or intrathecal injection.
9. The method of claim 2, wherein said kappa receptor antagonist binds reversibly.
10. The method of claim 2, wherein said kappa receptor antagonist binds irreversibly.
11. The method of claim 2, wherein said kappa receptor antagonist is nor-binaltorphimine.
12. The method of claim 2, wherein said kappa receptor antagonist is GNTI.
13. The method of claim 2, wherein said kappa receptor antagonist is DIPPA.
14. A method for reducing cAMP response element-binding protein (CREB) activation in the brain of a patient in need thereof comprising administering a kappa receptor antagonist.
15. The method of claim 14, wherein said kappa receptor antagonist is administered systemically.
16. The method of claim 14, wherein said kappa receptor antagonist is administered by intracerebroventricular or intrathecal injection.
17. The method of claim 14, wherein said kappa receptor antagonist binds reversibly.
18. The method of claim 14, wherein said kappa receptor antagonist binds irreversibly.
19. The method of claim 14, wherein said kappa receptor antagonist is nor-binaltorphimine.
20. The method of claim 14, wherein said kappa receptor antagonist is GNTI.
21. The method of claim 14, wherein said kappa receptor antagonist is DIPPA.

* * * * *